United States Patent [19]

Gallegra

[11] 3,988,365

[45] Oct. 26, 1976

[54] RESOLUTION OF 2-(6-METHOXY-2-NAPTHYL)PROPIONIC ACID

[75] Inventor: Pasquale Gallegra, San Jose, Calif.

[73] Assignee: Syntex Corporation, Panama, Panama

[22] Filed: Jan. 13, 1975

[21] Appl. No.: 540,376

Related U.S. Application Data

[63] Continuation-in-part of Ser. No. 350,193, April 11, 1973, abandoned, which is a continuation-in-part of Ser. No. 246,461, April 12, 1972, abandoned.

[52] U.S. Cl. ................. 260/520 D; 260/DIG. 8; 260/284
[51] Int. Cl.[2] ................. C07B 21/00; C07B 19/00; C07C 51/42
[58] Field of Search .......... 260/520 D, DIG. 8, 284; 350/193

[56] References Cited
UNITED STATES PATENTS

| | | | |
|---|---|---|---|
| 3,683,015 | 8/1972 | Dyson | 260/520 D |
| 3,904,683 | 9/1975 | Day et al. | 260/520 D |

OTHER PUBLICATIONS

Gilman, "Org. Chem.," Wiley & Sons, Inc., N.Y. (1958) pp. 256–258.

*Primary Examiner*—Norman Morgenstern
*Attorney, Agent, or Firm*—Joseph I. Hirsch; William B. Walker

[57] ABSTRACT

Resolution of mixtures of d and 1,2-(6-methoxy-2-napthyl)propionic acid with cinchonidine to yield the d-isomer is conducted by using, in combination with the cinchonidine, an inorganic base having a basicity, pKa, greater than 8 and forming a salt of 2-(6-methoxy-2-napthyl)propionic acid more soluble than the solubility of the corresponding cinchonidine salts. After the cinchonidine salt product is cleaved by treatment with a strong base at about room temperature in methanol, the methanolic solution is mixed with sufficient water to precipitate the cinchonidine in a form which is easy to filter. After removal of the precipitated cinchonidine, acidification yields a product enriched in d 2-(6-methoxy-2-napthyl)propionic acid.

18 Claims, No Drawings

RESOLUTION OF 2-(6-METHOXY-2-NAPTHYL)PROPIONIC ACID

CROSS-REFERENCE TO PARENT APPLICATIONS

This application is a continuation-in-part application of application Ser. No. 350,193, filed Apr. 11, 1973, which, in turn, was a continuation-in-part application of application Ser. No. 246,461, filed Apr. 12, 1972, both now abandoned.

SUMMARY OF THE INVENTION

This invention relates to a method for resolving mixtures of d and l 2-(6-methoxy-2-naphthyl)propionic acid to yield mixtures containing a higher proportion of the d-isomer.

In summary, the process for resolving mixtures of d and l 2-(6-methoxy-2-naphthyl)propionic comprises the steps of:

a. preparing a mixture of cinchonidine, a mixture of d and l 2-(6-methoxy-2-naphthyl)propionic acid, an inert organic solvent in which the cinchonidine salt of l 2-(6-methoxy-2-naphthyl)propionic acid is more soluble than the cinchonidine salt of d 2-(6-methoxy-2-naphthyl)propionic acid, and an inorganic base having a basicity, pKa, greater than 8, the solubility in the inert organic solvent of the salts of d and l 2-(6-methoxy-2-naphthyl)propionic acid and said inorganic base being more soluble than the cinchonidine salts of d and l 2-(6-methoxy-2-naphthyl)propionic acid; and b. crystallizing the cinchonidine salts of 2-(6-methoxy-2-naphthyl)propionic acid from the mixture to yield a salt mixture enriched in the salt of d 2(6-methoxy-2-naphthyl)propionic acid.

This procedure can be followed by one or more purifications to increase the purity of the d-isomer. Finally, the salt is cleaved to yield d 2-(6-methoxy-2-naphthyl)-propionic acid.

The 2-(6-methoxy-2-naphthyl)propionic acid and methods for its preparation are described, for example, in U.S. application Ser. No. 176,740 now abandoned, filed Aug. 31, 1971; and U.S. Pat. Nos. 3,651,106; 3,652,683; 3,658,858; 3,658,863; 3,663,584; and 3,686,238. One such method involves the reaction of a 1-halo-2-methoxynaphthalene with acetyl chloride in nitrobenzene in the presence of 3 molar equivalents of aluminum chloride to yield the corresponding 2-acetyl-5-halo-6-methoxynaphthalene derivative. The resulting derivative is heated with morpholine in the presence of sulfur at 150° C., and the resulting product is refluxed with concentrated hydrochloric acid to furnish the corresponding 2-naphthylacetic acid derivative. The latter compound is then esterified such as by reacting it with an alkanol in the presence of boron trifluoride, and the ester is treated with an alkali metal hydride in an ether solvent and then with an alkyl halide such as methyl iodide to yield the corresponding 2-(6-methoxy-2-naphthyl)propionate. The latter is hydrolyzed, for example, in an aqueous basic solution, to yield a mixture of the d- and l-isomers of 2-(6-methoxy-2-naphthyl)propionic acid.

The inorganic base used in the process of this invention has a basicity, pKa, greater than 8. The solubility in the inert organic solvent of the salts of the inorganic base and d and l 2-(6-methoxy-2-naphthyl)propionic acid must be greater than the solubility of the cinchonidine salts of d and l 2-(6-methoxy-2-naphthyl)propionic acid. Suitable inorganic bases include alkali metal hydroxides and carbonates such as potassium, sodium and lithium hydroxides and carbonates. The particular choice of inorganic base will depend upon the particular inert organic solvent system used for the crystallization. The selection of the best inorganic base in the process can be routinely determined by applying the above criterion. With methanol as the solvent, potassium hydroxide is the presently preferred inorganic base.

The inert organic solvent system for the process of this invention can use any inert organic solvent in which the cinchonidine salt of l 2-(6-methoxy-2-naphthyl)propionic acid and inorganic base salts of 2-(6-methoxy-2-naphthyl)propionic acid are soluble. Examples of such solvents include acetone, acetylacetone, adiponitrile, benzonitrile, benzylalcohol, benzyl mercaptan, butyl alcohol, capryl alcohol, diacetone alcohol, mono- and di(lower) alkyl ethers of ethylene glycol and diethylene glycol, ethanol, methanol, n-propanol, i-propanol, ethylene glycol, 1,2-propylene glycol, 1,3-propylene glycol, 2-ethylhexanol, dimethylsulfoxide, sulfolanes, dimethylformamide, N-methylpyrrolidinone, formamide, furfuryl alcohol, glycerol, isoamyl alcohol, isoamyl sulfide, isobutyl mercaptan, dibutoxytetraethylene glycol, pyridine, trimethylene glycol, dioxane, dimethylacetamide, and the like. The presently preferred solvents are polar and are not acidic or strongly basic.

The mixture should preferably contain about equal molar amounts of the 2-(6-methoxy-2-naphthyl)propionic acid and bases, including both cinchonidine and the inorganic base. The molar ratio of cinchonidine to inorganic base is not critical for resolution to occur. Cinchonidine to inorganic base molar ratios of 2:3–3:2 are operable, for example. For optimum quality and quantity yields of d 2-(6-methoxy-2-naphthyl)propionic acid, the molar ratio of cinchonidine and inorganic base should be about 1:1. At lower cinchonidine to inorganic base molar ratios, the quality of the product is not impaired but the quantity or yield rapidly decreases. With higher cinchonidine to inorganic base ratios, the quantity or yield is satisfactory, but the quality is impaired.

In general, resolution by crystallization is achieved by mixing the d and l 2-(6-methoxy-2-naphthyl)propionic acids, cinchonidine, inorganic base and sufficient solvent to solubilize the components, yielding a suspension of predominantly cinchonidine salt of d 2-(6-methoxy-2-naphthyl)propionic acid in nearly saturated solution of the other components, cooling the mixture, and separating the crystallized salts. Continued cooling causes continued further crystallization of the dissolved salts. Preferably, the solution is seeded with small quantities of the cinchonidine salt of d 2-(6-methoxy-2-naphthyl)propionic acid during the cooling since this ensures good resolution and high yields of the desired salt of the d-isomer. The initial and final temperatures of the solvent are chosen primarily by practical considerations as long as the temperature will not significantly degrade the other components. For example, the mixture can have an initial temperature of from 50° to 100° C and can be cooled to a final temperature lower than the initial temperature, e.g. less than 40° C, preferably about 35° C, over a period of hours, for example 4–12 hours, the temperature difference being sufficient to provide a high yield of crystals. The crystallizing mixture is maintained at the lower temperatures until crystallization is complete or nearly so, usually for longer than 15 minutes and preferably over 4.5 hours. The crystals are separated from the resultant mixture, for example, by filtration.

The quality or percentage of the d-isomer in the product can be increased, if desired, by purifications of the above-obtained crystals using the same solvents used in the initial crystallization or with different solvents as found desirable, the recrystallization being generally carried out as described above.

The combined mother liquors from each of the crystallization steps can be reprocessed. Either one or several recrystallizations can be carried out, depending upon the product purity required.

The salt product is cleaved with any organic or inorganic acid not destructive to the product to yield the d-isomer enriched 2-(6-methoxy-2-naphthyl)propionic acid. Alternatively, according to the presently preferred technique, the cleavage of the cinchonidine salt product can be effected by treating the salt product with a strong base, such as, for example, potassium hydroxide or other strong base having a pKa value greater than 10, followed by acidification, such as with hydrochloric acid or acetic acid, to give d 2-(6-methoxy-2-naphthyl)propionic acid. After the cinchonidine moiety is cleaved with the organic base in methanol, the resultant mixture is mixed with sufficient water to precipitate the cinchonidine in a form which is easy to filter. The ratio of water to methanol is at least about 3:1 (w/w), generally about 3:1 (w/w) to about 6:1 (w/w), for example, 3.6:1 (w/w) [corresponding to 3:1 (w/v) water-methanol mixture]. When conducted at room temperature, foaming of the reaction mixture (which occurs when the alkaline suspension of cinchonidine is heated to 83°–86° C) is avoided and the product is easy to filter. These advantages are attained, for example, with the 3.6:1 (w/w) water-methanol mixture utilized in Example 7 below, although higher ratios of water to methanol can be utilized, if desired, with similar results.

The cleavage step is considered to be an improvement over the ethyl acetate/hydrochloric acid cleavage of Dyson (U.S. Pat. No. 3,683,015). Although the Dyson technique does in fact, cleave the cinchonidine moiety from the remainder of the molecule, numerous lengthy extractions and back extractions are presently required, distillation of a mixed solvent system (ethyl acetate and isopropanol) is needed which limits solvent recovery and, in general, there are material losses encountered when the process is run on pilot plant or production-run scale. To overcome this problem, it was suggested to conduct the cleavage step with a strong base. When this suggestion was adopted, it was found that the cleavage step resulted in the formation of a fine crystalline precipitate of cinchonidine which would not be filtered. When the alkaline suspension of cinchonidine was heated to coagulate the fine precipitate, undesirable foaming resulted. To overcome these disadvantages, Applicant suggested that the methanolic solution be mixed with sufficient water to precipitate the cleaved cinchonidine. This step forms a cinchonidine precipitate which is easy to filter, thereby eliminating the need to heat the alkaline suspension of cinchonidine with its attendant undesirable foaming.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE 1

A mixture is prepared by adding, to a one liter flask, 70 g. (0.305 g. mole) of dl 2-(6-methoxy-2-naphthyl)-propionic acid, 44 g. (0.150 g. mole) of cinchonidine, 8.67 g. (0.155 g. mole) of potassium hydroxide and 220 ml. of methanol. These ingredients were stirred, and the mixture is refluxed for 4 hours. The mixture is then gradually cooled to 25° C. over five hours and maintained at that temperature for a further 12 hours. The resultant suspension is then filtered, and the solids are washed with 100 ml. of methanol and dried at 50°–55° C. The yield of cinchonidine salt of d 2-(6-methoxy-2-naphthyl)propionic acid is about 90% (w/w). $[\alpha]_D = 57°$ –58° (of the liberated acid).

EXAMPLE 2

Repeating the procedure of Example 1 but replacing 8.67 g. of potassium hydroxide with 7.6 g. (0.136 g. moles) of potassium hydroxide also yields an improved yield of cinchonidine salt of d 2-(6-methoxy-2-naphthyl)propionic acid compared with that obtainable using 100 percent cinchonidine.

EXAMPLE 3

Repeating the procedure of Example 1 but replacing potassium hydroxide with sodium hydroxide, potassium carbonate, and sodium carbonate, yields, in each case, an improved yield of cinchonidine salt of d 2-(6-methoxy-2-naphthyl)propionic acid compared with that obtainable using 100 percent cinchonidine.

EXAMPLE 4

A 65 g. portion of cinchonidine salt of d 2-(6-methoxy-2-naphthyl)propionic acid ($[\alpha]_D = 58.8°$; of the liberated acid) is mixed with 195 ml. methanol, and the mixture is stirred and refluxed for 4 hours. The solution is cooled to 25° C over five hours and filtered. The filtrate is washed with 30 ml. of methanol having a temperature of 25° C. and dried at 45°–50° C. The yield of the cinchonidine salt of d 2-(6-methoxy-2-naphthyl)propionic acid is about 95.2% (w/w). $[\alpha]_D = 66.1°$ (of the liberated acid).

EXAMPLE 5

The product of Example 4 (61.8 g.) is mixed with 450 ml. of ethyl acetate and 300 ml. of dilute hydrochloric acid (5:1 v/v water to acid). The ethyl acetate layer is then filtered, and the ethyl acetate is replaced with isopropanol by distilling while adding incremental amounts of isopropanol. The product is mixed with water, cooled to 20° C., filtered, and the residue is washed with water to yield d 2-(6-methoxy-2-naphthyl)propionic acid. $[\alpha]_D = 66.1°$.

EXAMPLE 6

To a suitably sized vessel containing potassium hydroxide (61.8 kg.) dissolved in methanol (1557 l) there is charged dl 2-(6-methoxy-2-naphthyl)propionic acid (500 kg.) with constant stirring. Cinchonidine (315 kg.) is added and the batch heated under reflux for about four hours. After cooling at a rate of 8° C. per hour to 25°–30° C. and aging for 5 hours the batch is filtered and the filter cake washed with methanol (1418 l.). The wet filter cake is charged in methanol (144 l.) to a second suitably sized vessel and heated under reflux for four hours. After cooling at a rate of 8° C. per hour to 25°–30° C. the batch is filtered and the cake (d-cinchonidine salt) washed with methanol (450 l.). The yield of the cinchonidine salt of d 2-(6-methoxy-2-naphthyl)propionic acid (d-cinchonidine salt) is about 86–92% w/w.

EXAMPLE 7

To a suitably sized vessel containing potassium hydroxide (54 kg.) dissolved in methanol (730 l.) there is charged d-cinchonidine salt wet cake (455 kg.), obtained as described in Example 6. After stirring for 20 minutes at 20°–25° C. under nitrogen, water (2080 l.) is added and the stirring continued for a further 2 hours. The ratio of water to methanol in this step corresponds to about 3.6:1 (w/w). The precipitated cinchonidine is filtered off and the filter cake washed with water. The combined filtrate and wash is extracted with chloroform (3 × 416 l.). The aqueous layer is then charged with hydrochloric acid (125 kg.) in water (794 l.) and warmed to 35°–40° C. under vacuum to remove any chloroform. The batch is cooled to 25° C., aged for one hour, and d 2-(6-methoxy-2-naphthyl)propionic acid filtered off and washed with water.

EXAMPLE 8

Acetone (2000 l.), the wet cake of d 2-(6-methoxy-2-naphthyl)propionic acid of Example 7 and activated carbon (e.g., Darco G-60) are charged to a suitably sized vessel and the mixture stirred for 5 minutes. The batch is filtered and the filter cake washed with acetone. The combined filtrate and washings are vacuum distilled to a volume of 1000 l. and cooled to 25°–30° C. Water (3000 l.) is charged, and the batch aged for 30 minutes at 5°–0° C. and the precipitated d 2-(6-methoxy-2-naphthyl)propionic acid filtered off, washed with water and dried at about 45°–50° C. The yield of d 2-(6-methoxy-2-naphthyl)propionic acid is 34–38% w/w.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A process for resolving 2-(6-methoxy-2-naphthyl)propionic acid comprising the steps of:
   a. preparing a mixture of cinchonidine, an inorganic base selected from the group consisting of alkali metal hydroxides and alkali metal carbonates, said inorganic base having a basicity, pKa, of greater than 8, d and l 2-(6-methoxy-2-naphthyl)propionic acid and an inert organic solvent in which the cinchonidine salt of l 2-(6-methoxy-2-naphthyl)propionic acid and the inorganic base salts of d and l 2-(6-methoxy-2-naphthyl)propionic acid are soluble, the cinchonidine salt of l 2-(6-methoxy-2-naphthyl)propionic acid being more soluble in said organic solvent than is the cinchonidine salt of d 2-(6-methoxy-2-naphthyl)propionic acid, the inorganic base salts of d and l 2-(6-methoxy-2-naphthyl)propionic acid being more soluble in said inert organic solvent than are the cinchonidine salts of d and l 2-(6-methoxy-2-naphthyl)propionic acid,
   b. crystallizing the cinchonidine salts of d and l 2-(6-methoxy-2-naphthyl)propionic acid from the mixture to yield a salt product enriched in the cinchonidine salt of d 2-(6-methoxy-2-naphthyl)propionic acid, and
   c. treating said salt product enriched in the cinchonidine salt of d 2-(6-methoxy-2-naphthyl)propionic acid with a strong base at about room temperature in methanol, mixing the resultant mixture with water, removing precipitated cinchonidine, and acidifying the resultant water-methanol mixture to yield a product enriched in d 2-(6-methoxy-2-naphthyl)propionic acid.

2. The process of claim 1 wherein said inorganic base is an alkali metal hydroxide.

3. The process of claim 1 wherein said inorganic base is an alkali metal carbonate.

4. The process of claim 1 wherein said inorganic base is potassium hydroxide.

5. The process of claim 1 wherein the solvent is methanol.

6. The process of claim 1 wherein about equimolar quantities of (a) said d and l 2-(6-methoxy-2-naphthyl)propionic acid and (b) a mixture of said cinchonidine and said inorganic base are utilized, the molar ratio of cinchonidine to inorganic base in said mixture (b) being from 2:3 to 3:2.

7. The process of claim 6 wherein said molar ratio of cinchonidine to inorganic base in said mixture is about 1:1.

8. The process of claim 1 wherein said strong base is potassium hydroxide.

9. The process of claim 1 wherein said acidification is conducted with hydrochloric acid.

10. The process of claim 1 wherein the ratio of water to methanol in said water-methanol mixture is at least about 3:1 (w/w).

11. The process of claim 1 wherein the ratio of water to methanol in said water-methanol mixture is about 3:1 (w/w).

12. The process of claim 1 wherein the ratio of water to methanol in said water-methanol mixture is about 3.6:1 (w/w).

13. A process for cleaving the cinchonidine salt of d 2-(6-methoxy-2-naphthyl)propionic acid which comprises treating a salt product enriched in the cinchonidine salt of d 2-(6-methoxy-2-naphthyl)propionic acid with a strong base at about room temperature in a methanol, mixing the resultant mixture with water, removing precipitated cinchonidine, and acidifying the resultant water-methanol mixture to yield a product enriched in d 2-(6-methoxy-2-naphthyl)propionic acid.

14. The process of claim 13 wherein said strong base is potassium hydroxide.

15. The process of claim 13 wherein said resultant mixture is acidified with hydrochloric acid.

16. The process of claim 13 wherein the ratio of water to methanol in said water-methanol mixture at least about 3:1 (w/w).

17. The process of claim 13 wherein the ratio of water to methanol in said water-methanol mixture is about 3:1 (w/w).

18. The process of claim 13 wherein the ratio of water to methanol in said water-methanol mixture is about 3.6:1 (w/w).

* * * * *

UNITED STATES PATENT AND TRADEMARK OFFICE
CERTIFICATE OF CORRECTION

PATENT NO. : 3,988,365
DATED : October 26, 1977
INVENTOR(S) : Pasquale Gallegra

It is certified that error appears in the above-identified patent and that said Letters Patent are hereby corrected as shown below:

Page 1, in the paragraph designated [63], line 3, "April 12, 1972" should read -- April 21, 1972 --; and
Column 1, line 9, "April 12, 1972" should read -- April 21, 1972 --.

Signed and Sealed this

Eleventh Day of April 1978

[SEAL]

Attest:

RUTH C. MASON
*Attesting Officer*

LUTRELLE F. PARKER
*Acting Commissioner of Patents and Trademarks*